(12) United States Patent
Agard et al.

(10) Patent No.: US 11,033,312 B2
(45) Date of Patent: Jun. 15, 2021

(54) BIOMATERIAL DISPENSING DEVICE

(71) Applicant: GLOBUS MEDICAL, INC., Audubon, PA (US)

(72) Inventors: Ryan Agard, Royersford, PA (US); Sean Suh, Morganville, NJ (US); Damien O'Halloran, Conshohocken, PA (US); Michael Moretti, Pottstown, PA (US); Mark Weiman, Downingtown, PA (US); Chad Glerum, Pennsburg, PA (US)

(73) Assignee: Globus Medical, Inc., Audubon, PA (US)

( * ) Notice: Subject to any disclaimer, the term of this patent is extended or adjusted under 35 U.S.C. 154(b) by 126 days.

(21) Appl. No.: 16/378,610

(22) Filed: Apr. 9, 2019

(65) Prior Publication Data

US 2019/0231407 A1  Aug. 1, 2019

Related U.S. Application Data

(63) Continuation of application No. 15/078,060, filed on Mar. 23, 2016, now Pat. No. 10,292,748, which is a continuation of application No. 14/572,828, filed on Dec. 17, 2014, now Pat. No. 9,320,556, which is a continuation of application No. 14/051,872, filed on Oct. 11, 2013, now Pat. No. 8,939,985, which is a continuation of application No. 13/158,155, filed on Jun. 10, 2011, now Pat. No. 8,603,096.

(51) Int. Cl.
*A61B 17/88* (2006.01)
*B65D 83/00* (2006.01)
*G01F 11/02* (2006.01)
*A61B 90/00* (2016.01)
*A61B 17/00* (2006.01)

(52) U.S. Cl.
CPC ...... *A61B 17/8819* (2013.01); *A61B 17/8825* (2013.01); *A61B 17/8827* (2013.01); *B65D 83/0011* (2013.01); *G01F 11/027* (2013.01); *A61B 2017/0042* (2013.01); *A61B 2017/00473* (2013.01); *A61B 2017/00477* (2013.01); *A61B 2090/0813* (2016.02)

(58) Field of Classification Search
CPC .................. A61B 17/8825; A61B 17/8819
See application file for complete search history.

(56) References Cited

U.S. PATENT DOCUMENTS

| | | | |
|---|---|---|---|
| 4,583,974 A | 4/1986 | Kokemak | |
| 4,594,073 A | 6/1986 | Stine | |
| 4,994,065 A | 2/1991 | Gibbs et al. | |
| 5,071,040 A | 12/1991 | Laptewicz, Jr. | |
| 5,431,654 A | 7/1995 | Nic | |
| 5,893,488 A | 4/1999 | Hoag | |
| 6,383,190 B1 | 5/2002 | Preissman | |

(Continued)

FOREIGN PATENT DOCUMENTS

| EP | 1157677 A2 | 11/2001 |
|---|---|---|
| EP | 1400213 A1 | 3/2004 |

*Primary Examiner* — Andrew Yang

(57) ABSTRACT

A device for dispensing biomaterial includes a handle configured to receive a syringe, the syringe including a biomaterial and a threaded plunger, and an engagement pin retained within the handle and slidable between a first position and a second position. The engagement pin is configured to engage the threaded plunger in the first position, the engagement pin is further configured to disengage from the threaded plunger in the second position.

16 Claims, 12 Drawing Sheets

(56) References Cited

U.S. PATENT DOCUMENTS

| | | |
|---|---|---|
| 6,395,007 B1 | 5/2002 | Bhatnagar |
| 6,439,439 B1 | 8/2002 | Rickard |
| 6,582,439 B1 | 6/2003 | Sproul |
| 6,599,293 B2 | 7/2003 | Tague |
| 6,599,520 B2 | 7/2003 | Scarborough |
| 6,645,213 B2 | 11/2003 | Sand |
| 6,770,079 B2 | 8/2004 | Bhatnagar |
| 6,796,987 B2 | 9/2004 | Tague |
| 6,887,246 B2 | 5/2005 | Bhatnagar |
| 7,270,667 B2 | 9/2007 | Faccioli |
| 7,316,689 B2 | 1/2008 | Lieberman |
| 7,371,241 B2 | 5/2008 | Evans |
| 2004/0204715 A1 | 10/2004 | Evans et al. |
| 2004/0260304 A1 | 12/2004 | Faccioli et al. |
| 2005/0124997 A1 | 6/2005 | Pajunk et al. |

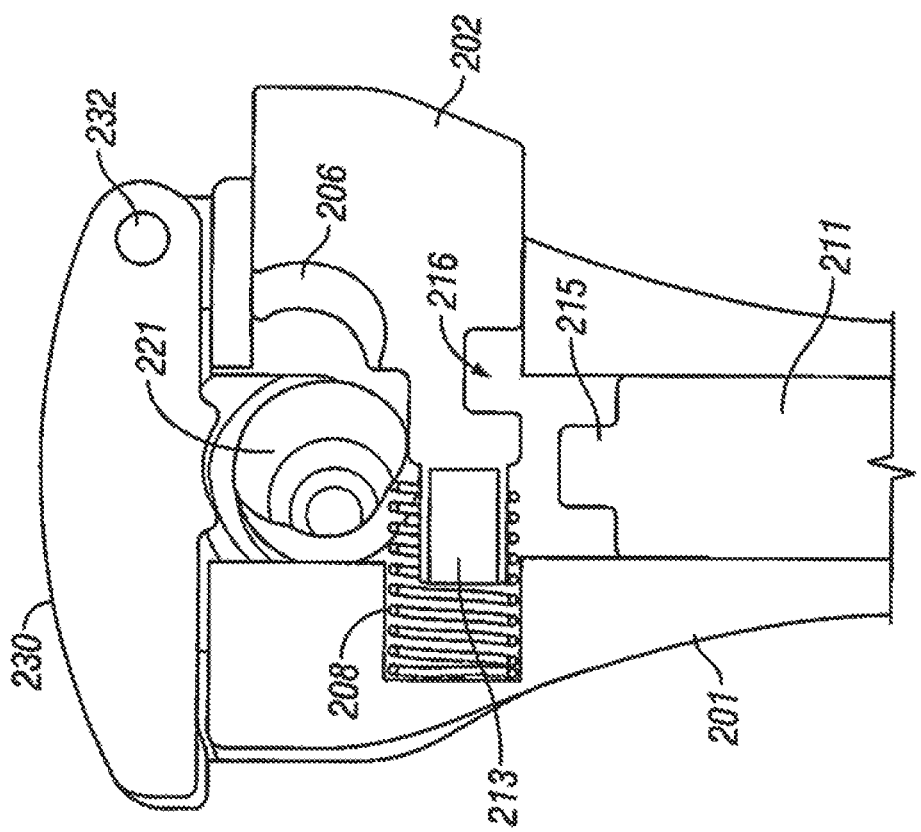
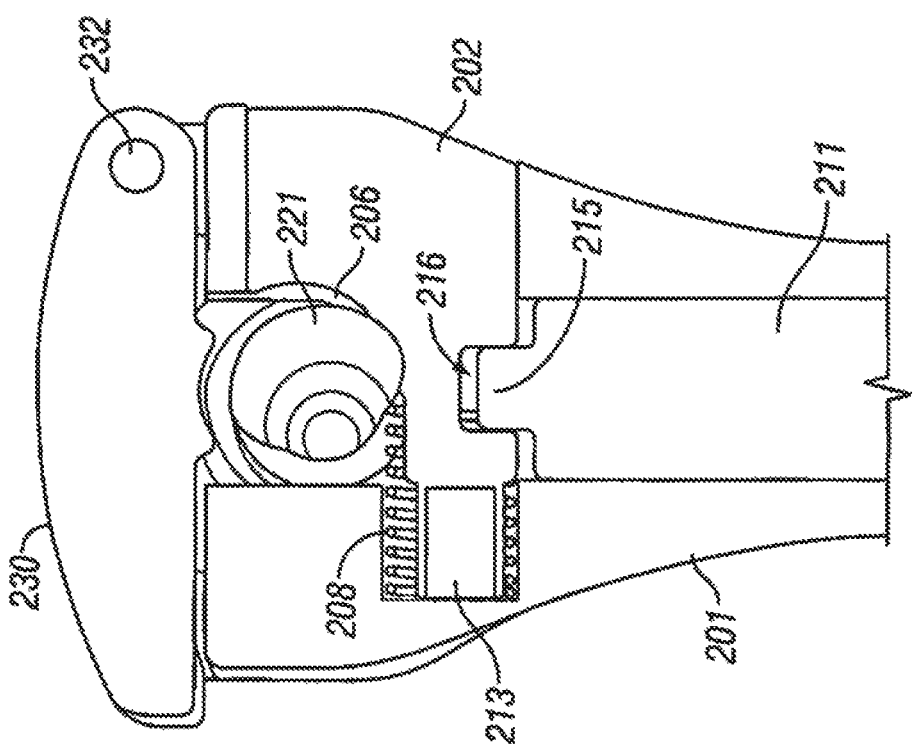

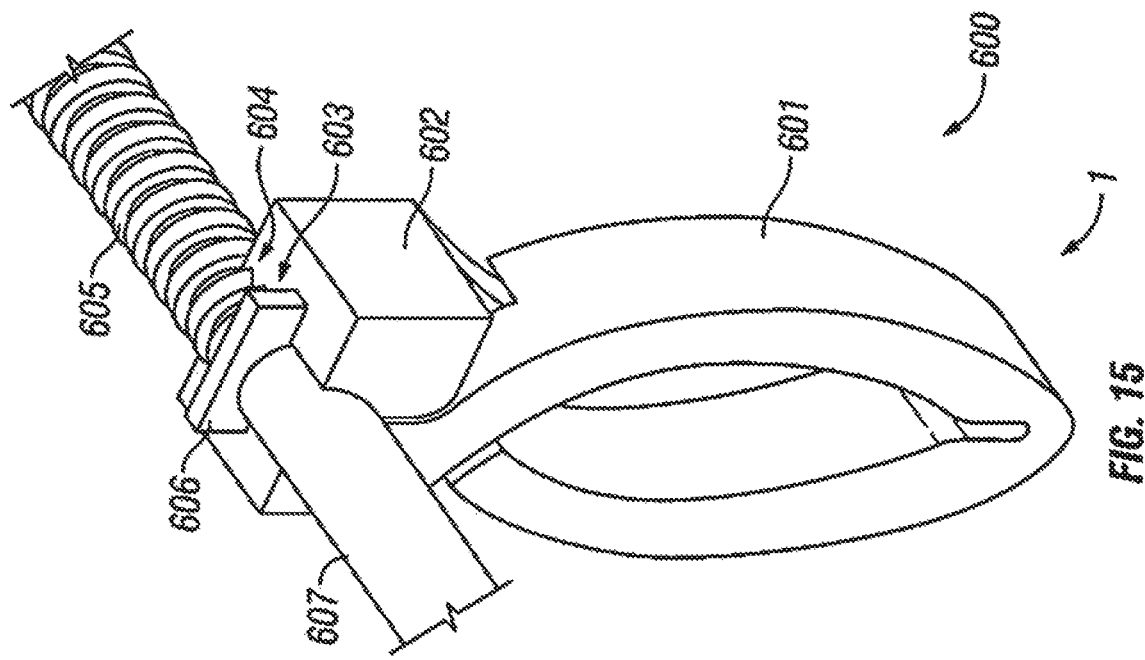
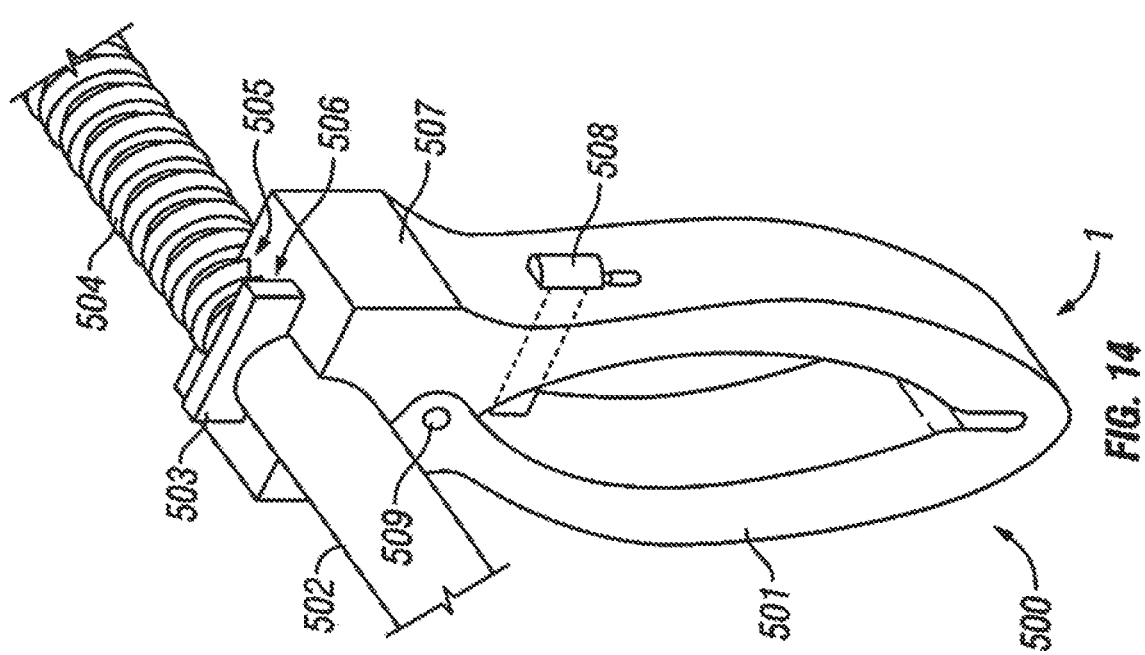

BIOMATERIAL DISPENSING DEVICE

CROSS REFERENCE TO RELATED APPLICATIONS

This patent application is a continuation of U.S. patent application Ser. No. 15/078,060, filed Mar. 23, 2016 (published as U.S. Pat. Pub. No. 2016-0199114), which is a continuation of U.S. patent application Ser. No. 14/572,828, filed Dec. 17, 2014, now U.S. Pat. No. 9,320,556, which is a continuation application of U.S. patent application Ser. No. 14/051,872, filed Oct. 11, 2013, now U.S. Pat. No. 8,939,985, which is a continuation application of U.S. patent application Ser. No. 13/158,155, filed Jun. 10, 2011, now U.S. Pat. No. 8,603,096, all of which are incorporated by reference in their entireties for all purposes.

BACKGROUND OF THE DISCLOSURE

1. Field of the Disclosure

The disclosure is directed to devices and methods for dispensing biomaterials such as for injecting bone cement, also known as poly(methyl methacrylate) or PMMA. In particular, the disclosure is directed to a cement gun for injecting bone cement. Bone cement is often injected to secure prosthetic devices, such as, e.g., artificial joints and spinal fusion constructs, to natural bone.

2. Related Art

Many devices are available to assist a surgeon with injecting bone cement to secure a prosthesis. These devices, however, suffer from one or more flaws. For example, some devices are single-use and may not be re-sterilized, increasing surgical costs.

Some devices are incompatible with interchangeable syringe assemblies. If the surgeon uses all the cement in the device, she must halt the surgical procedure while she mixes additional cement. To avoid this, the surgeon may have a second device ready. Either solution increases surgical costs.

Moreover, some syringe assemblies may have inadequate configurations for securing the syringe assembly. When using these devices, the syringe assembly may unexpectedly fall out of the device, adding additional complications to an already difficult procedure.

Many devices lack mechanisms for relieving injection pressure in the syringe. When a device does have such a mechanism, it is usually difficult to operate. Quick relief of injection pressure is critical for safety during a surgical procedure. Bone cement hardens by a polymerization reaction that releases heat. Droplets of bone cement that contact soft tissue can result in burns and other injuries that may add additional complications to an invasive surgical procedure. Preventing stray droplets of bone cement may substantially reduce or eliminate the burn danger posed by bone cement. A surgeon may prevent stray droplets by reducing injection pressure in the syringe. If the mechanism for reducing injection pressure is clumsy or difficult to operate, the surgeon may not be able to prevent stray droplets of bone cement from falling onto soft tissues. Other complications, such as, e.g., over-filling a cavity or fracture, may also result from clumsy or complicated pressure-relief mechanisms. In contrast, a mechanism for quickly and easily reducing injection pressure may help the surgeon improve the safety of the procedure by, e.g., preventing stray droplets.

Accordingly, there is a need for a device that is compatible with an interchangeable syringe assembly and provides an easy-to-use mechanism for quickly relieving injection pressure in the syringe.

SUMMARY OF THE DISCLOSURE

The disclosure meets the foregoing need and allows use of an interchangeable syringe assembly and provides a quick release mechanism to relieve injection pressure, which results in a significant increase in safety during a surgical procedure and other advantages apparent from the discussion herein.

Accordingly, in one aspect of the disclosure a device for dispensing biomaterial includes a handle configured to receive a syringe, the syringe including a biomaterial and a threaded plunger, and an engagement pin retained within the handle and slidable between a first position and a second position, the engagement pin configured to engage the threaded plunger in the first position, the engagement pin further configured to disengage from the threaded plunger in the second position.

The device may include a hole in the handle, the hole may be configured to hold the engagement pin, the hole may be located so as to permit a user of the device to ergonomically slide the engagement pin between the first position and the second position. The device may include a locking pin configured to retain the engagement pin within the hole, and at least one ball plunger configured to releasably hold the engagement pin in at least one of the first position and the second position. The device may include a lid having a closed position and an open position, the lid may be configured to retain the syringe within the handle in the closed position, the lid further may be configured to release the syringe from the handle in the open position, a hinge pin may be configured to connect the lid to the handle, and at least one ball plunger may be configured to releasably hold the lid in the closed position. The device may include a lid having a closed position and an open position, the lid may be configured to retain the syringe within the handle in the closed position, the lid further may be configured to release the syringe from the handle in the open position, a hinge pin may be configured to attach the lid to the handle, a lid pin may be located in a side of the lid and may be configured to fit into a corresponding hole in the handle, thereby retaining the lid in the closed position, and a lid spring may be configured to press the lid in a direction substantially parallel to the lid pin axis, the spring further may be configured to retain the lid pin in its corresponding hole until released by a user of the device. The device may include the lid spring being a coil spring, and the lid spring may surround at least a portion of the hinge pin. A method for opening the lid of the device may include sliding the lid along the hinge pin to compress the lid spring, the sliding resulting in extraction of the lid pin from its corresponding hole, rotating the lid about the hinge pin so that the lid pin is not aligned with its corresponding hole, and sliding the lid along the hinge pin until the lid spring is no longer compressed. The method may include placing the engagement pin in the second position, placing the syringe into the handle, sliding the engagement pin to the first position to engage the threaded plunger, dispensing biomaterial, and relieving injection pressure in the syringe by sliding the engagement pin to the second position.

According to another aspect of the disclosure, a device for dispensing bone cement includes a handle configured to receive a syringe, the syringe including a biomaterial and a threaded plunger, an engagement mechanism contained within the handle and having a first position and a second position, the engagement mechanism configured to engage the threaded plunger in the first position, the engagement mechanism further configured to disengage from the threaded plunger in the second position, a locking mechanism configured to releasably lock the engagement mechanism in the first position, and a release button configured to disengage the locking mechanism, thereby releasing the engagement mechanism from the first position, the release button located so as to permit a user of the device to ergonomically disengage the locking mechanism.

The locking mechanism may include a clutch mechanism. The device may include an engagement mechanism spring configured to press the engagement mechanism toward the second position. The locking mechanism may include a locking pin. The device may include a locking pin spring configured to press the locking pin toward the engagement mechanism. The engagement mechanism may include a slot, and the locking pin may include a blade configured to engage the slot in the engagement mechanism when the engagement mechanism is in the first position. The release button may be configured to disengage the blade from the slot. The device may include a lid having a closed position and an open position, the lid may be configured to retain the syringe within the handle in the closed position, the lid further may be configured to release the syringe from the handle in the open position, a hinge pin may be configured to connect the lid to the handle, and at least one ball plunger may be configured to releasably hold the lid in the closed position. The device may include a lid having a closed position and an open position, the lid may be configured to retain the syringe within the handle in the closed position, the lid further configured to release the syringe from the handle in the open position, a hinge pin may be configured to attach the lid to the handle, a lid pin may be located in a side of the lid and may be configured to fit into a corresponding hole in the handle, thereby retaining the lid in the closed position, and a lid spring may be configured to press the lid in a direction substantially parallel to the lid pin, the spring further configured to retain the lid pin in its corresponding hole until released by a user of the device. The lid spring may be a coil spring, and the lid spring may surround at least a portion of the hinge pin.

A method for opening the lid of the device when the lid pin is inserted into its corresponding hole may include sliding the lid along the hinge pin to compress the lid spring, the sliding resulting in extraction of the lid pin from its corresponding hole, rotating the lid about the hinge pin so that the lid pin is not aligned with its corresponding hole, and sliding the lid along the hinge pin until the lid spring is no longer compressed. A method may include placing the engagement mechanism in the second position, placing the syringe into the handle, moving the engagement mechanism to the first position, locking the engagement mechanism in the first position with the locking mechanism, dispensing biomaterial, and relieving injection pressure in the syringe by operating the release button.

Additional features, advantages, and embodiments of the disclosure may be set forth or apparent from consideration of the following detailed description, drawings, and claims. Moreover, it is to be understood that both the foregoing summary of the disclosure and the following detailed description are exemplary and intended to provide further explanation without limiting the scope of the disclosure as claimed.

BRIEF DESCRIPTION OF THE DRAWINGS

The accompanying drawings, which are included to provide a further understanding of the disclosure, are incorporated in and constitute a part of this specification, illustrate embodiments of the disclosure and together with the detailed description serve to explain the principles of the disclosure. No attempt is made to show structural details of the disclosure in more detail than may be necessary for a fundamental understanding of the disclosure and the various ways in which it may be practiced. In the drawings:

FIG. 9A shows a cross-section view of the cement gun of FIG. 4 with the engagement mechanism in an engaged position;

FIG. 9B shows a cross-section view of the cement gun of FIG. 4 with the engagement mechanism in a disengaged position;

FIGS. 14 and 15 show further clutch mechanisms according to aspects of the disclosure.

DETAILED DESCRIPTION OF THE DISCLOSURE

Figure 1:
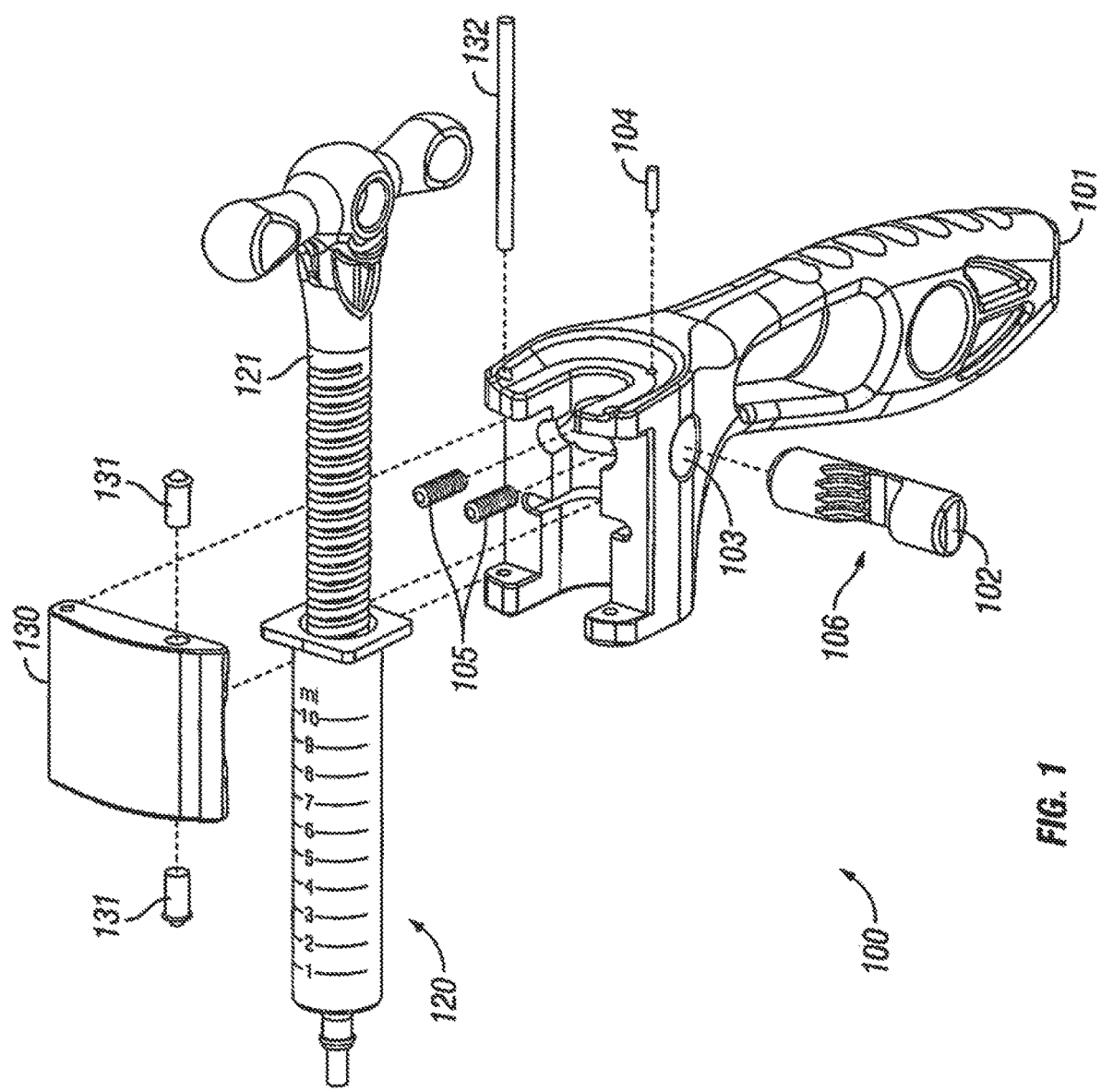
FIG. 1 shows an exploded view of a cement gun, according to an aspect of the disclosure.

The embodiments of the disclosure and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure, which is defined solely by the appended claims and applicable law. Moreover, it is noted that like reference numerals represent similar parts throughout the several views of the drawings.

FIG. 1 shows an exploded view of an aspect of the disclosure. According to this aspect of the disclosure, a cement gun 100 may include a handle 101 and an engagement pin 102 that fits into a hole 103 in the handle 101. The handle 101, engagement pin 102, and related parts may be made of titanium; steel, including surgical stainless steel; metal; plastic; or a like material that allows the cement gun 100 to be repeatedly sterilized. The components of cement gun 100 may be coated or treated to be antibacterial, antimicrobial, or the like.

The engagement pin 102 may be retained in the handle with a locking pin 104 that fits into a groove (not shown) in the engagement pin 102. The locking pin 104 may be permanently affixed to the handle 101 by, e.g., welding, epoxy, adhesive, glue, compression, riveting, or the like. The mating of the locking pin 104 to the groove permits the engagement pin 102 to travel from side-to-side while still being retained within the handle 101.

In particular, the engagement pin 102 may travel back-and-forth between an engaged position and a disengaged position, described in detail below. To prevent or reduce the likelihood of the engagement pin 102 shifting between these positions except when so desired by the user, the handle 101 may incorporate two ball plungers 105. The ball plungers 105 may include a ball and spring construction. The ball plungers 105 may be aligned with one of two notches 107 (shown in FIGS. 3B, 3C) in the underside of the engagement pin 102. For example, the ball plunger 105 associated with the engaged position of the engagement pin 102 may engage the notch 107 associated with the engaged position. This engagement may retain the engagement pin 102 in the engaged position, preventing it from spontaneously shifting to a different (i.e. disengaged) position. When the engagement pin is, e.g., in the engaged position, the ball plunger 105 associated with the disengaged position is not aligned with the notch 107 associated with the disengaged position.

Handle 101 may receive a syringe assembly 120, which may include a threaded plunger 121. The handle 101 may also be fitted with a lid 130 to secure and retain the syringe assembly 120. The lid 130 may have a secure closure for retaining the syringe assembly 120 within the handle. According to an aspect of the disclosure, the lid 130 may be attached to the handle 101 with a hinge pin 132. The hinge pin 132 creates an axis of rotation along one side of the lid 130. The axis is such that the lid 130 may be rotated up and away from the handle 101 to permit easy and quick removal and/or insertion of a syringe assembly 120. The lid 130 may then be rotated down to a closed position for use.

As shown in FIG. 1, the lid 130 may be fitted with two ball plungers 131 on corners distant from the hinge pin 132, although more or fewer ball plungers may be used without departing from the spirit and scope of the disclosure and claims. The ball plungers may include a ball and a spring construction. When the lid 130 is in a closed position, the ball plungers 131 may align with notches, cutouts, holes, or the like (not shown) in the handle 101. The ball plungers 131 may retain the lid 130 in the closed position during normal use and operating conditions.

Figure 3B:
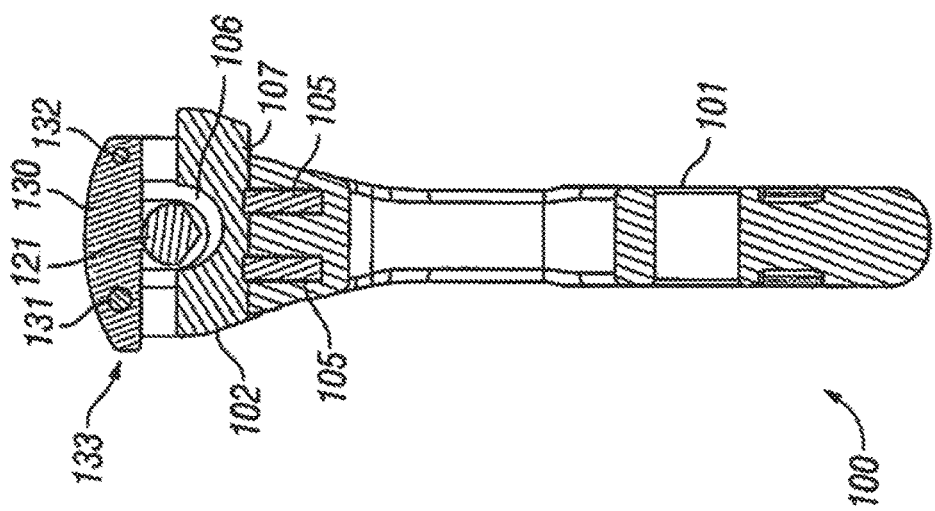
FIG. 3B shows a cross-section view of the cement gun of FIG. 3A along line B-B with the engagement pin in a disengaged position.
Figure 3A:
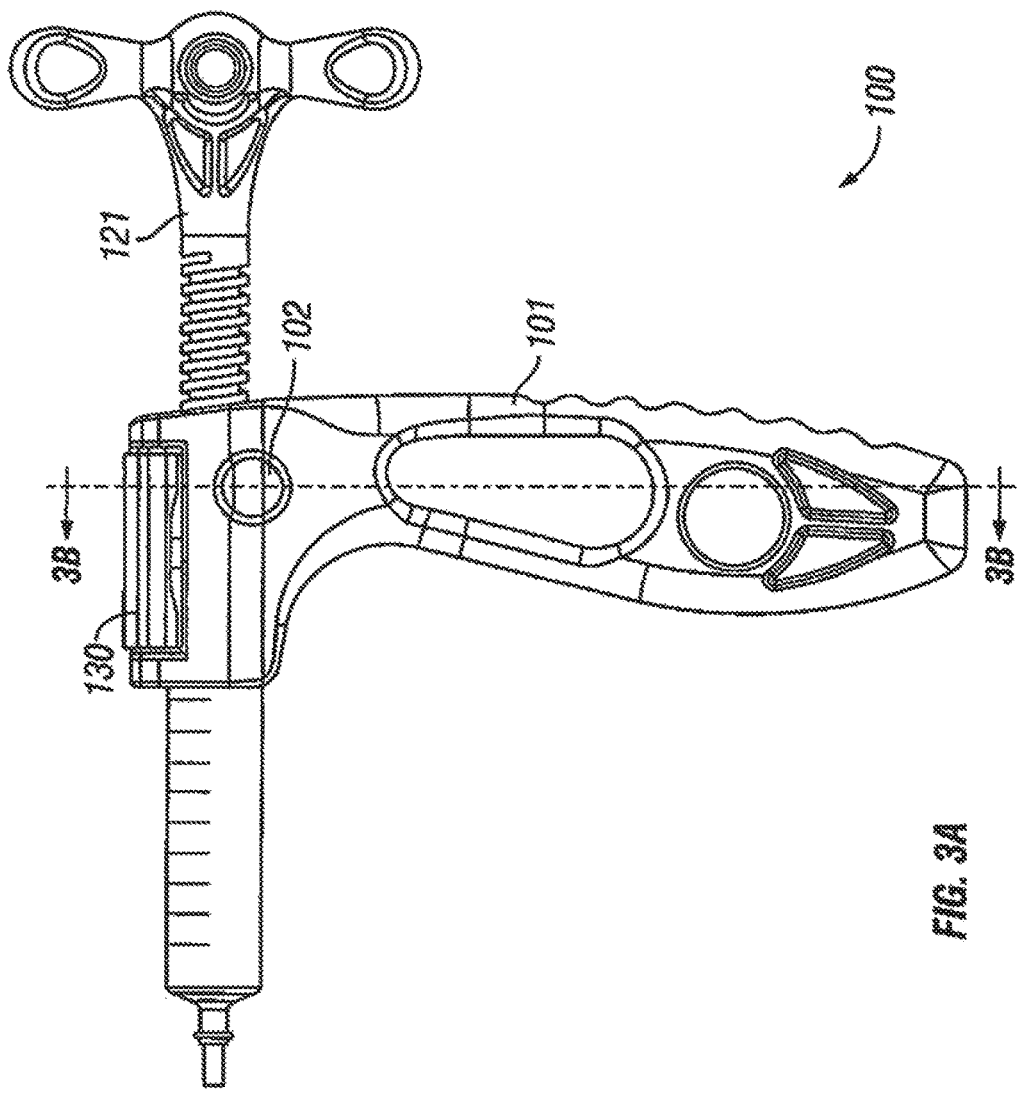
FIG. 3A shows a side view of the cement gun of FIG. 1.

To facilitate opening the lid 130, the lid 130 may have an overhang or lip 133 on the side opposite the lid hinge 132 (shown in FIGS. 3A, 3B). This lip or overhang 133 may provide purchase or leverage, making it easier for a user to open the lid 130 than it would be if the edge of the lid was more flush with the side of the handle.

According to an alternate aspect of the disclosure, handle 101 may be fitted with the push-type lid as described below with respect to FIGS. 4, 5A, 5B, and 5C.

Figure 2:
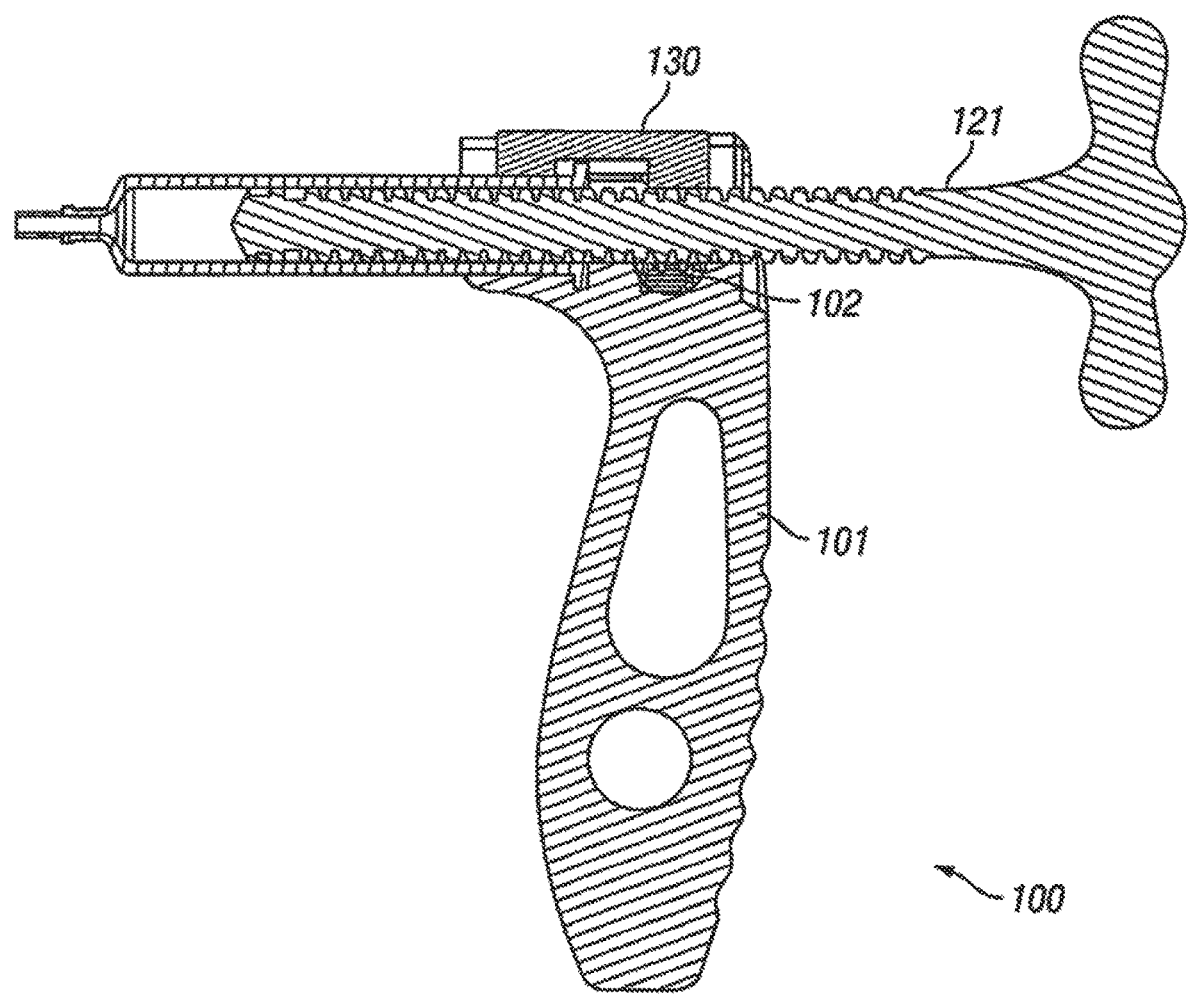
FIG. 2 shows a cutaway view of the cement gun of FIG. 1.
Figure 3C:
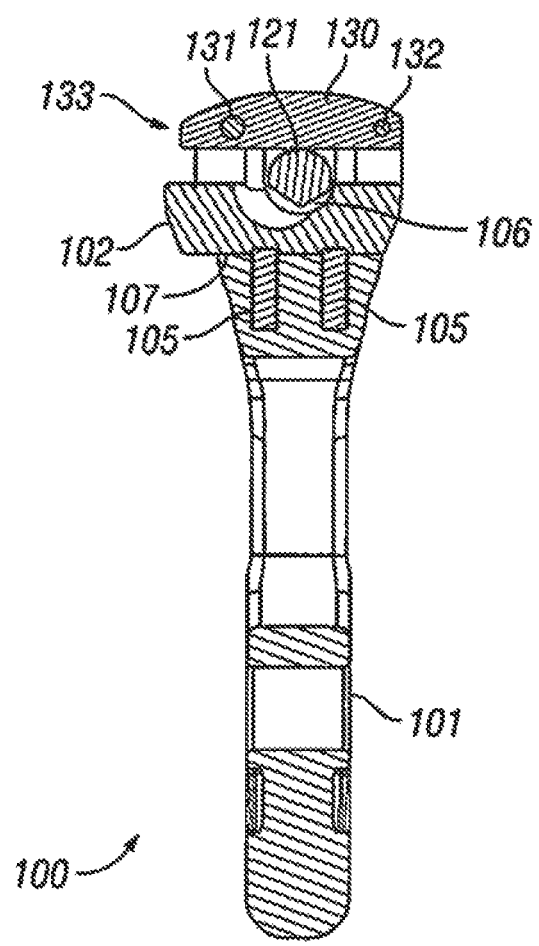
FIG. 3C shows a cross-section view of the cement gun of FIG. 3A along line B-B with the engagement pin in an engaged position.

FIG. 2 shows a cross-section view of the cement gun 100, while FIG. 3A shows an external side view of the cement gun 100. FIG. 3B shows a cutaway view taken along line B-B in FIG. 3A with the engagement pin 102 in a disengaged position. FIG. 3C shows a cross-section view taken along line B-B in FIG. 3A with the engagement pin in an engaged position. Engagement pin 102 contains a cutout 106 with one or more grooves that may be structured and arranged to engage the threads of the threaded plunger 121 of the syringe assembly 120. As shown in FIG. 1, the grooves are only located along one side of the cutout 106. When the engagement pin 102 is in a disengaged position, as shown, e.g., in FIG. 3B, the grooves do not engage the threaded plunger 121. When the engagement pin 102 is in an engaged position, as shown, e.g., in FIG. 3C, the grooves engage the threads of the plunger 121. Since the syringe 120 contains no mating threads of its own for the plunger 121, the plunger 121 can only be advanced by twisting when it is seated in the handle 101 and the engagement pin 102 is in an engaged position.

Since bone cement can be a very viscous material, it may be necessary to create substantial pressure inside the syringe assembly to force the bone cement through the narrow opening in the syringe. A surgeon or other user of the cement gun may create this pressure by placing the engagement pin 102 in an engaged position and turning the handle of the threaded plunger 121 until a desired flow of bone cement is achieved. If it becomes necessary to cease the flow of bone cement for any reason, the user may simply slide the engagement pin to the disengaged position. Since there are no other groves or threads holding the plunger in position, the pressure inside in the syringe assembly 120 may cause the plunger to slide partially out of the syringe, thereby relieving the injection pressure and stopping the flow of bone cement.

As shown in FIGS. 1, 2, and 3A, the engagement pin 102 may be located just above the grip of handle 101. This provides a location for the engagement pin 102 that may be very ergonomic for users of the cement gun 100. In this sense and as used herein, "ergonomic" and "ergonomically" mean that the elements are designed so as to minimize or reduce a user's physical effort and discomfort, thereby maximizing or improving efficiency. For example, a right-handed user of the cement gun 100 as shown in FIG. 3C may be able to easily slide the engagement pin 102 from the engaged position to the disengaged position with a simple movement of his thumb. A left-handed user may be able to disengage the engagement pin 102 with her index finger. The index finger, however, may not be as effective at disengaging the pin 102 as the thumb. Depending on the force required to disengage pin 102, it may be desirable to provide a left-handed model of the cement gun 100 with the grooves on the opposite side of cutout 106. This configuration may permit a left-handed surgeon and other user to disengage the engagement pin 102 with his thumb.

Figure 4:
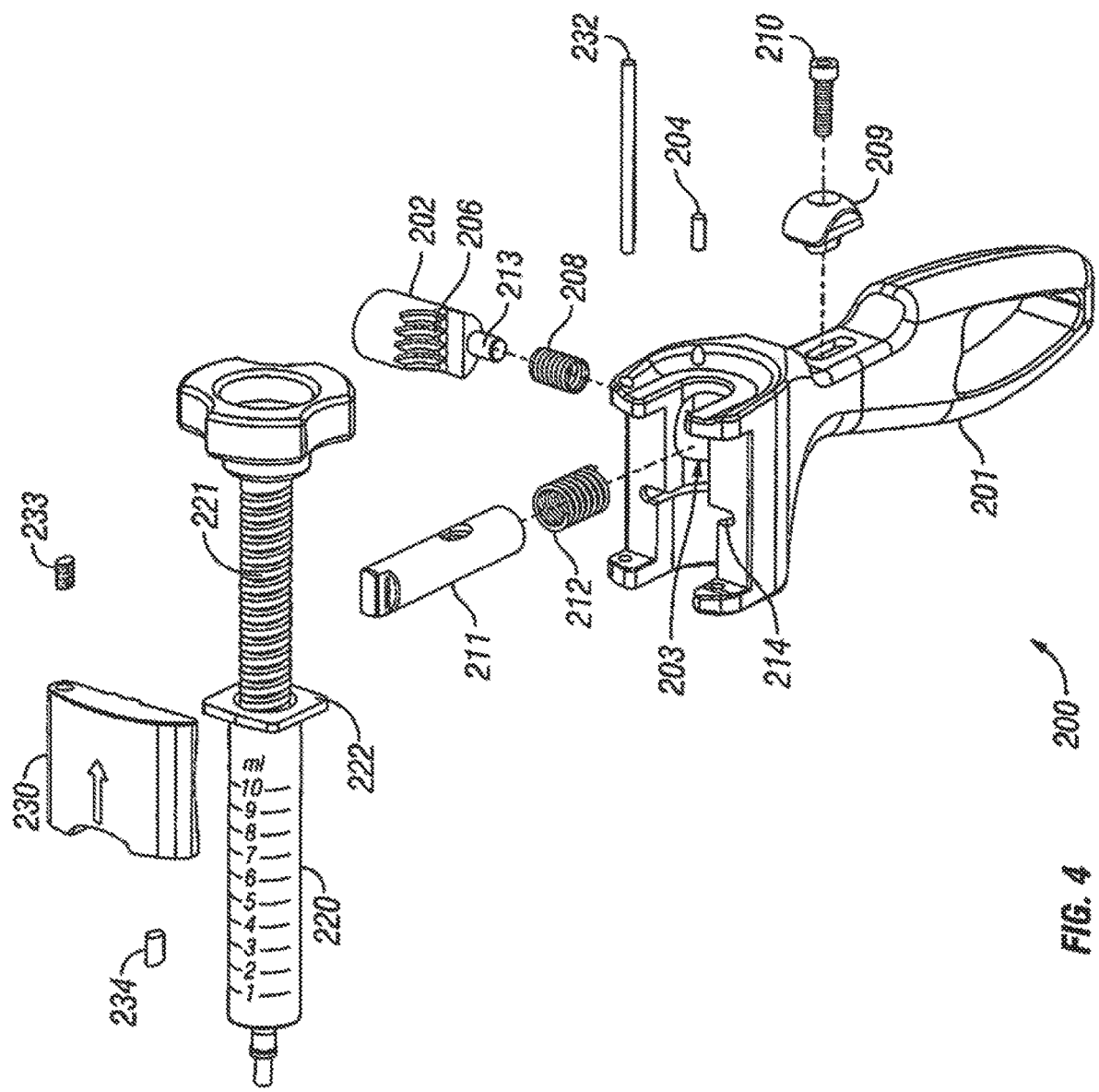
FIG. 4 shows an exploded view of a cement gun according to an alternate aspect of the disclosure.

FIG. 4 shows an exploded view of a cement gun of an alternate aspect of the disclosure. According to this aspect, a cement gun 200 may include a handle 201 and an engagement mechanism 202. The engagement mechanism 202 may fit into a hole 203 in the handle 201. The handle 201, engagement mechanism 202, and related parts may be made of titanium; steel, including surgical stainless steel; metal; plastic; or a like material that allows the cement gun 200 to be repeatedly sterilized. The components of cement gun 200 may be coated or treated to be antibacterial, antimicrobial, or the like.

The engagement mechanism 202 may be retained in handle 201 with a dowel pin 204 that fits into a groove (not shown) in the engagement mechanism 202. The dowel pin 204 may be permanently affixed to the handle 201 by, e.g., welding, epoxy, adhesive, glue, compression, riveting, or the like. The mating of the dowel pin 204 to the groove permits the engagement mechanism 202 to travel from side-to-side while still being retained within the handle 201.

The engagement mechanism 202 may be retained in an engaged position by a locking mechanism, such as, e.g., a locking pin 211. The engagement mechanism 202 may be disengaged by using a release button 209 to release the locking mechanism. The engagement mechanism 202 may include a cutout with one or more grooves or threads 206. The engagement mechanism 202 may be mated with a spring 208 to press or bias the engagement mechanism 202 toward a disengaged position. Spring 208 may be held in place with a retaining pin 213, which may fit into a corresponding hole or socket (not shown) in handle 201.

Handle 201 may receive a syringe assembly 220, which may include a threaded plunger 221. The handle 201 may also be fitted with a lid 230 to secure and retain the syringe assembly 220. A lid 230 with a secure closure is critical for retaining the syringe assembly 220 within the handle. According to an aspect of the disclosure, a lid 230 may be attached to the handle 201 with a hinge pin 232. The hinge pin 232 creates an axis of rotation along one side of the lid 239. The axis is such that the lid 230 may be rotated up and away from the handle 201 to permit easy and quick removal and/or insertion of a syringe assembly 220. The lid 230 may then be rotated down to a closed position for use.

As shown in FIG. 4, lid 230 may include a lid pin 234 along one side of the lid 230. Lid pin 234 may be inserted into a corresponding hole or socket (not shown) in handle 201 to retain lid 230 in a closed position. A user may insert lid pin 234 into its corresponding socket by first placing lid 230 in a closed position, with pin 234 aligned with its hole, and then sliding lid 230 in the direction of the lid pin 234 and its hole. To keep lid pin 234 in its hole and keep lid 230 in a closed position, a spring 233 may press against lid 230 to press or bias the lid 230 in the direction of lid pin 234 and its hole. Spring 233 may be a coil spring and may be fitted over hinge pin 232 such that hinge pin 232 passes through the interior diameter of the coil.

Figures 5A, 5B, 5C:
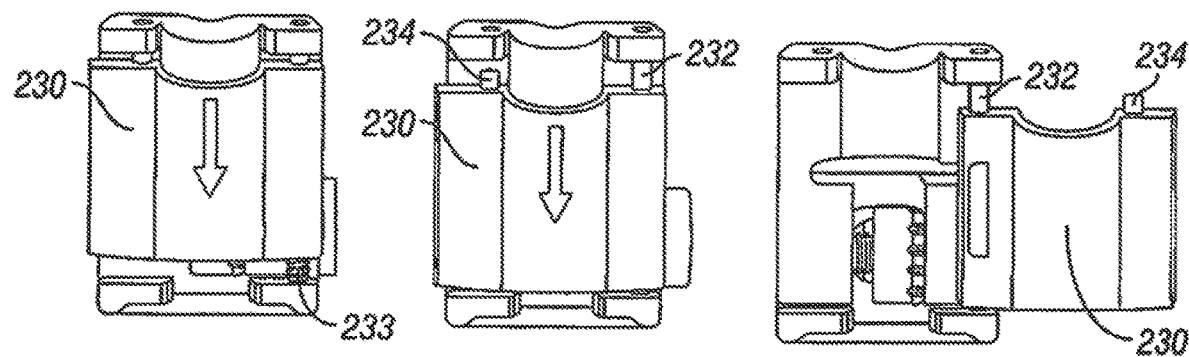
FIGS. 5A, 5B, and 5C show the operation of the lid of the cement gun of FIG. 4.

FIGS. 5A, 5B, and 5C show steps for opening lid 230. In FIG. 5A, lid 230 is in a closed position, with lid pin 234 inserted into its corresponding hole or socket. The user of the cement gun 200 slides the lid away from pin 234. As shown in FIG. 5B, spring 233 may be compressed in the process. Lid pin 234 is now clear of its hole, and lid 230 may be rotated to an open position, such as shown in FIG. 5C.

According to an alternate aspect of the disclosure, handle 201 may be fitted with a ball plunger-type lid as described above with respect to FIG. 1.

Figure 6:
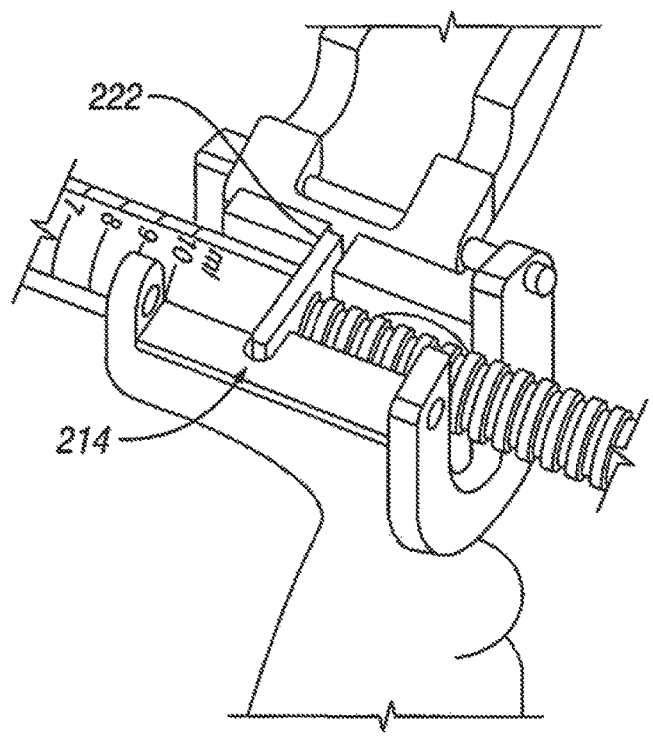
FIG. 6 shows the cradle of the cement gun of FIG. 4.

FIG. 6 shows how a flange 222 of the syringe assembly 220 that may fit into the cradle 214 of the handle 201.

Figure 7B:
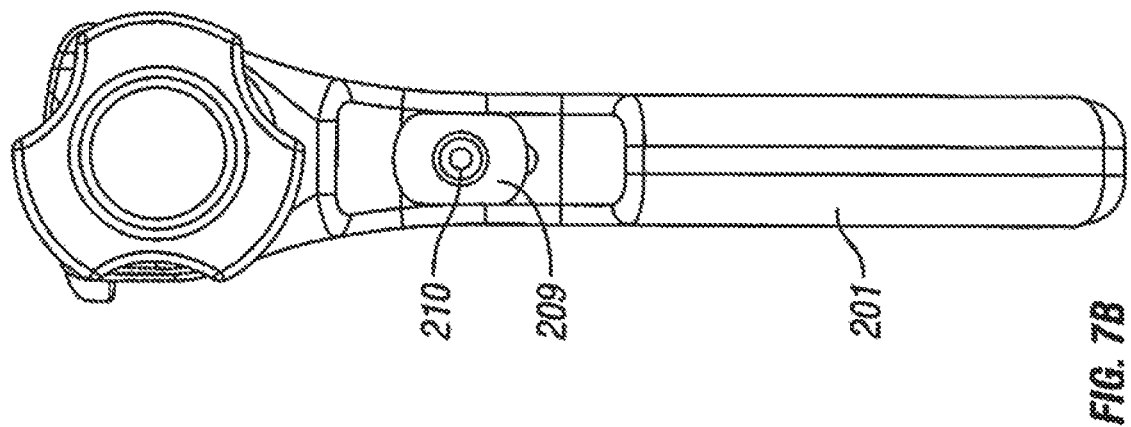
FIGS. 7A and 7B show a cross-section view and rear view, respectively, of the cement gun of FIG. 4 with the engagement mechanism in an engaged position.
Figure 7A:
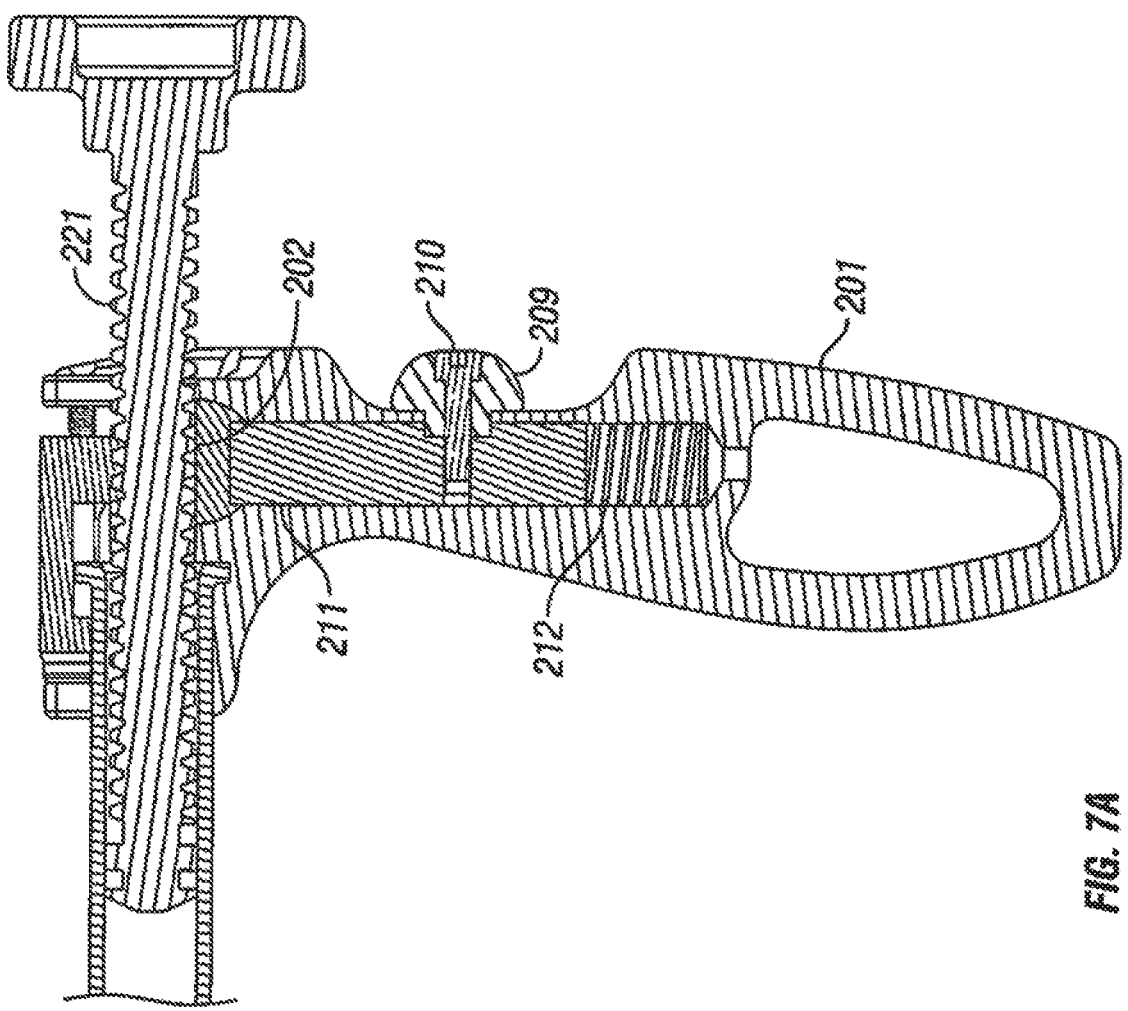

FIG. 7A shows a cross-section view of the cement gun 200 with the engagement mechanism 202 locked in the engaged position by the locking mechanism, in this case a locking pin 211. FIG. 7B shows a rear view of the cement gun 200 of FIG. 7A. With the engagement mechanism 202 in the engaged position, the groove or threads 206 in the cutout are meshed with the threads on the threaded plunger 221 of the syringe assembly 220. The locking mechanism in this aspect of the disclosure is a locking pin 211 with a flat portion or blade 215 at its uppermost end. The blade 215 fits into a groove 216 in the bottom of the engagement mechanism 202, locking the engagement mechanism 202 into place in the engaged position. A release button 209 is affixed to the rear of the handle 201 and connected to the locking pin 211 with a screw 210, although other means of connecting the release button 209 to the locking pin are contemplated and are within the spirit and scope of the disclosure. A spring 212 may be located beneath the locking pin 211 to press or bias the locking pin 211 toward the engagement mechanism 202.

Figure 8B:
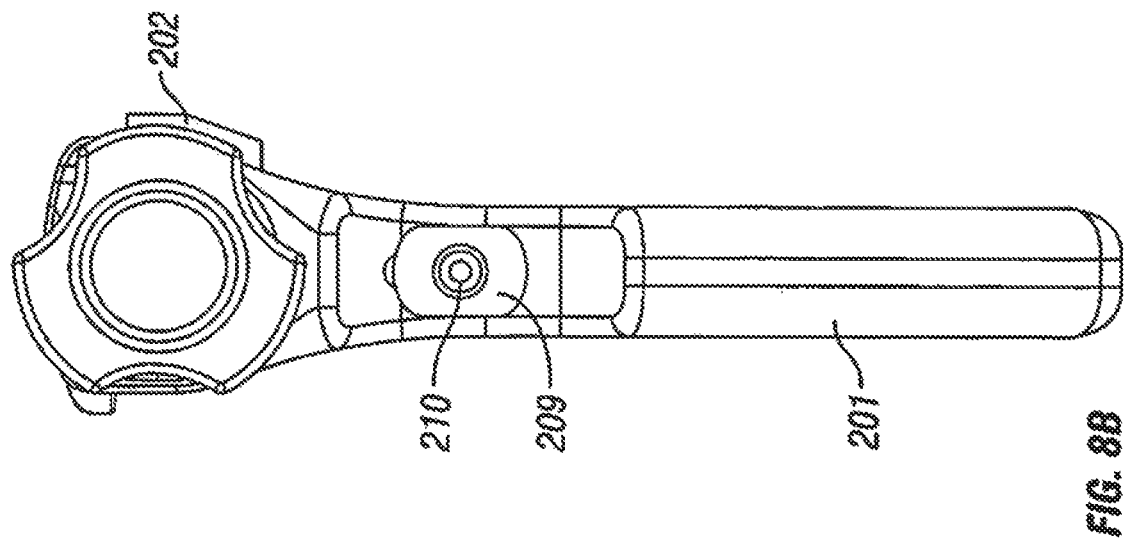
FIGS. 8A and 8B show a cross-section view and rear view, respectively, of the cement gun of FIG. 4 with the engagement mechanism in a disengaged position.
Figure 8A:
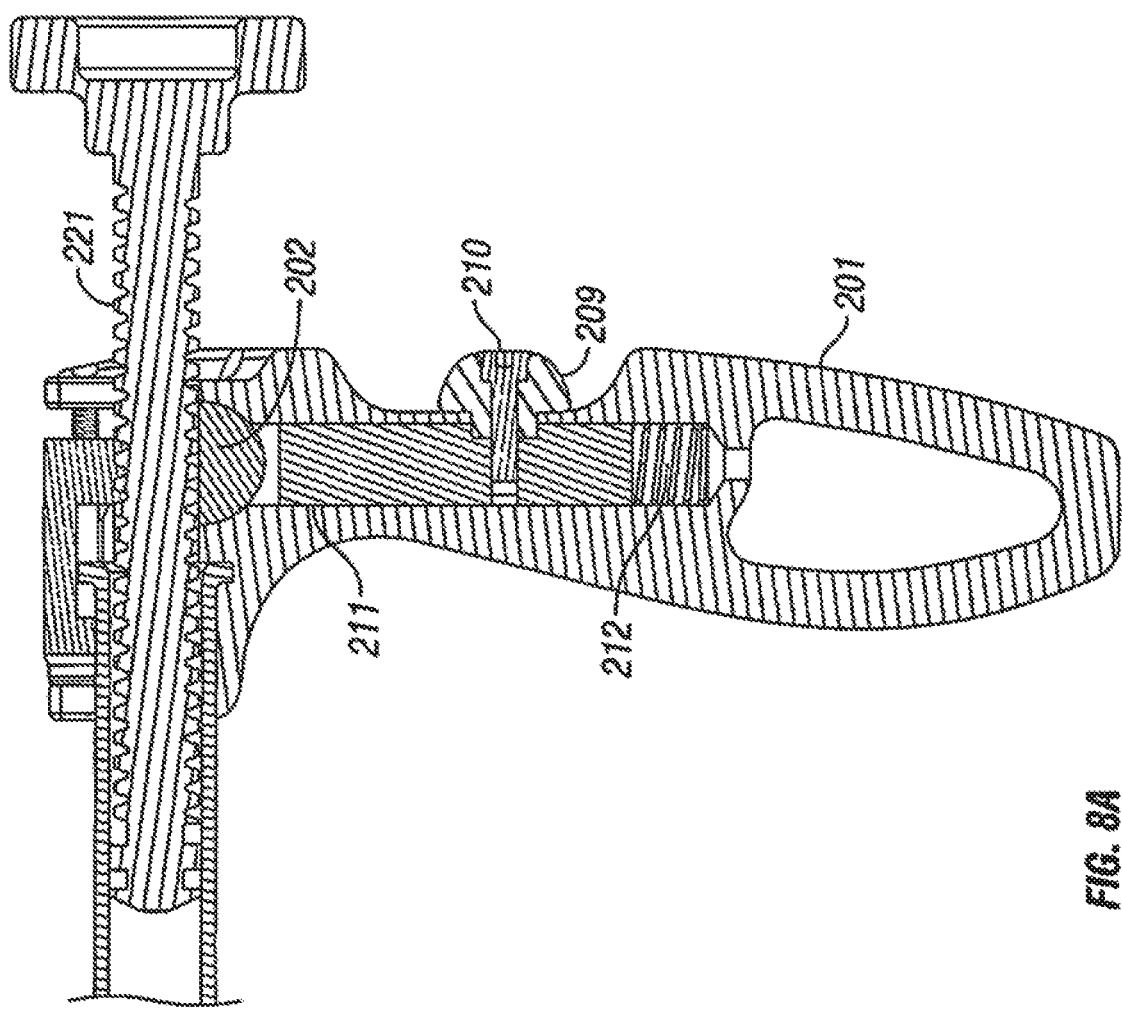

FIG. 8A shows a cutaway view of the cement gun 200 with the locking pin 211 disengaged from the engagement mechanism 202, and FIG. 8B shows a rear view of the cement gun 200 of FIG. 8A. To release the engagement mechanism from the engaged position, a surgeon or other user of the cement gun 200 may slide the release button 209 downward, e.g., to the position shown in FIGS. 8A and 8B. Since the release button 209 is connected to the locking pin 211, the locking pin also moves down until the blade 215 is clear of its groove 216 in the underside of the engagement mechanism 202. In some aspects, the engagement mechanism 202 may have a spring 208 to bias the mechanism 202 away from the engaged position and toward a disengaged position. Thus, when the blade 215 is fully removed from its groove 216, the engagement mechanism may snap or pop to a disengaged position. Disengaging locking pin 211 compresses spring 212, which in turn biases or presses locking pin 211 toward or against the underside of the engagement mechanism 202. When engagement mechanism 202 is returned to an engaged position and the blade 215 aligns with its groove 216 in the engagement mechanism 202, spring 212 may press locking pin 211 upward so that the blade 215 engages the groove 216 and locks the engagement mechanism 202 in the engaged position.

Release button 209 may be ergonomically located on the handle 201, as shown e.g. in FIGS. 7A, 7B, 8A, and 8B. In this configuration, the user of the cement gun 200 may disengage the locking mechanism by sliding the release button 209 down with his thumb. This configuration may be operated with equal efficiency by both right-handed and left-handed users.

FIGS. 9A and 9B show rear cross-section views of the locking pin 211 and engagement mechanism 202 in locked and unlocked positions, respectively. In FIG. 9A, the threads or grooves 206 of the engagement mechanism 202 are meshed with the threads of the threaded plunger 221. Spring 208 is compressed, pressing or biasing mechanism 202 away from its current, engaged, position. The engagement mechanism 202, however, is held in the engaged position by virtue of the blade 215 of the locking pin 211, which is inserted into groove 216 on the underside of the engagement mechanism 202. With the parts in this configuration, the surgeon or user of the cement gun 200 may increase injection pressure inside the syringe by turning the handle or knob of the threaded plunger 221.

If the user needs to quickly relieve the injection pressure, he simply slides the ergonomically located release button 209 down. Release button 209 is connected to locking pin 211 and thus moves the locking pin 211 downward as well. As shown in FIG. 9B, when the locking pin has traveled sufficiently downward, the blade 215 is removed from the groove 216. Spring 208 is now able to press the engagement mechanism 202 to the right, thereby disengaging threads 206 from threaded plunger 221. Spring 208 retains proper alignment with engagement mechanism 202 thanks to retaining pin 213.

Figure 10A:
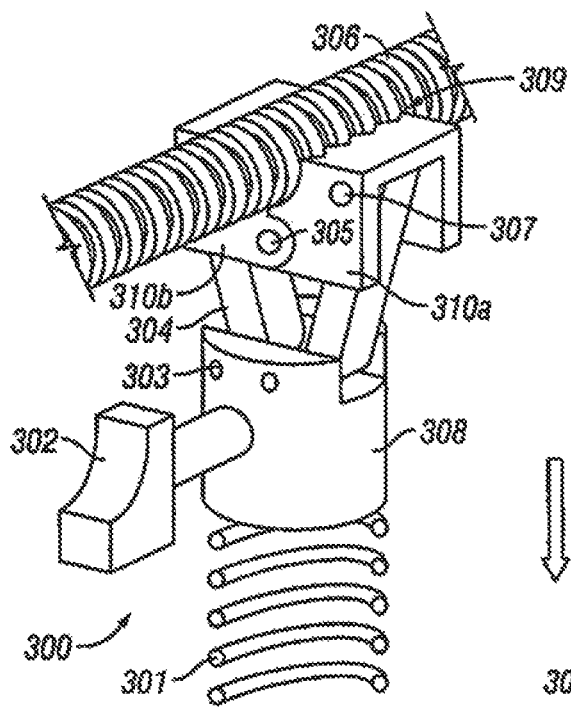
FIGS. 10A, 10B, 10C, and 10D show a clutch mechanism according to an additional aspect of the disclosure.
Figure 10B:
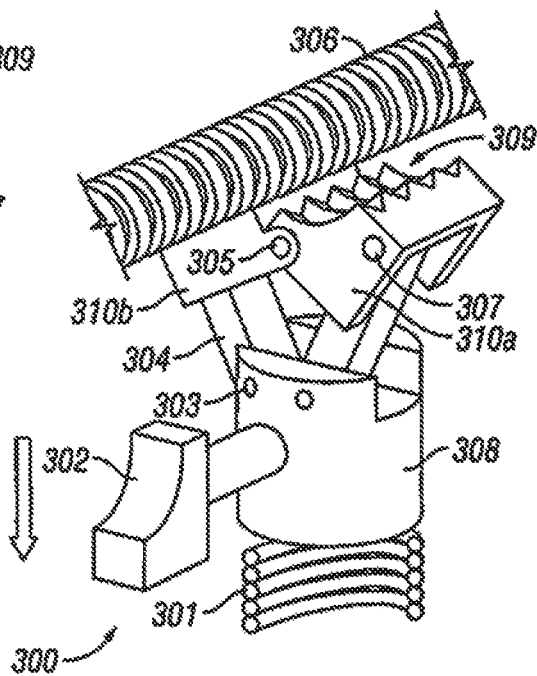
Figure 10C:
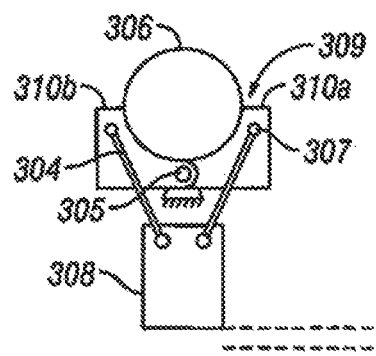
Figure 10D:
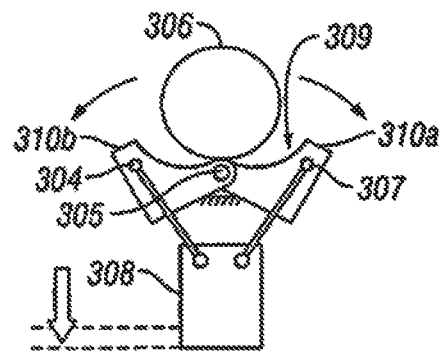

FIGS. 10A, 10B, 10C, and 10D show a clutch mechanism 300 that may be used as a locking mechanism for the cement gun 200 in place of the locking pin 211 described above. Clutch 300 may include a fixed pivot 305 that may be fixed in place relative to the threaded plunger 306. Fixed pivot 305 may join a pair of jaws 310a, 310b and allow them to rotate relative to one another. Jaws 310 are connected to arms 304 by pivots 307, and arms 304 are connected to clutch pin 308 by pivots 303. Clutch pin 308 may be biased or pressed upwards by spring 301. This upward pressure on clutch pin 308 translates into pressure to close jaws 310. Jaws 310 may include threads or grooves to engage threads on threaded plunger 306. In this way, jaws 310 provide the same function as engagement mechanism 202, as shown in FIGS. 10A and 10C. To open the jaws 310 and, e.g., quickly relieve injection pressure, a user may press down on release button 302. This motion compresses spring 301, moves pin 308 downwardly, and opens jaws 310, as shown in FIGS. 10B and 10D.

Figure 11A:
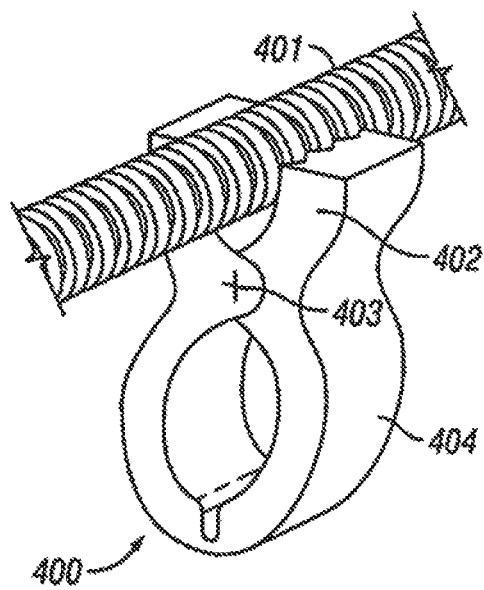
FIGS. 11A, 11B, 12, 13A, and 13B show additional clutch mechanisms according to aspects of the disclosure.
Figure 11B:
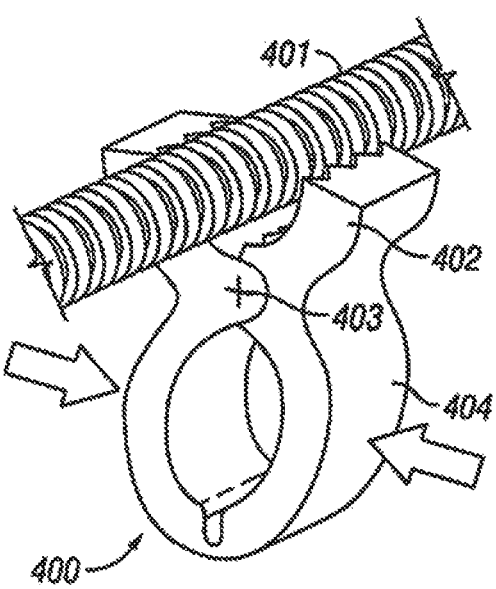
Figure 12:
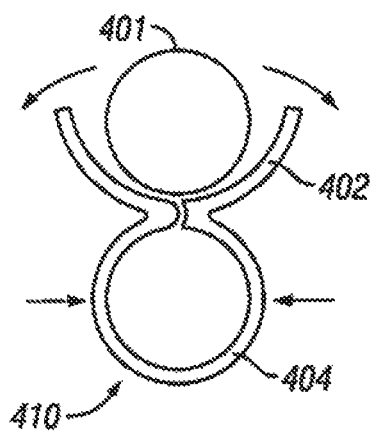
Figure 13A:
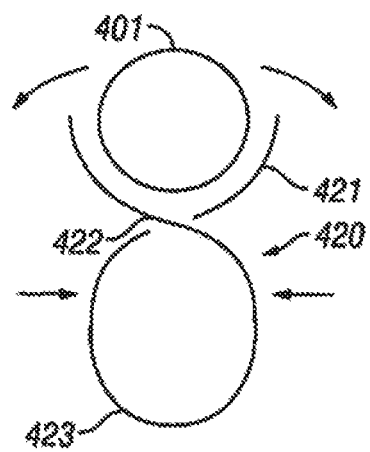
Figure 13B:
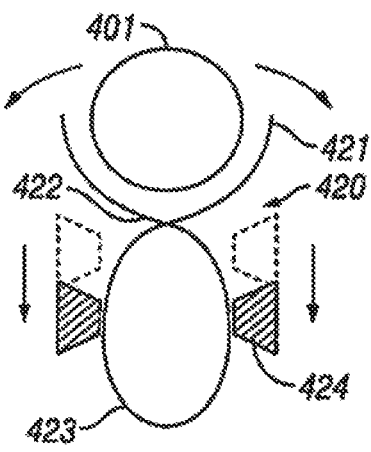

FIGS. 11A, 11B, 12, 13A, and 13B show alternate aspects of a clutch mechanism. Clutches 400, 410, and 420 are all naturally biased toward a closed or gripping position without an external spring, such as, e.g., spring 301. In FIG. 11A, clutch 400 has a central pivot 403. Pressing on the clutch loop 404, as shown in FIG. 11B, may cause the jaws 402 of clutch 400 to open, releasing its grip on threaded plunger 401. Clutch 410, shown in FIG. 12, is similar to clutch 400 but lacks the central pivot. As shown in FIG. 13A, Clutch 420 is formed from a continuous piece of material, such as metal, looped across itself, crossing at crossover point 422, to give the proper bias to the jaws 421. Clutch 420 may open its jaws 421 by compressing clutch loop 423, as for clutches 400 and 410. Alternatively, a sliding mechanism 424, as shown in FIG. 13B, may have the same effect compress loop 423. All three clutch types are compatible with a release button mechanism, similar in operation to those shown for cement gun 200 and clutch 300, as will be understood by one having ordinary skill in the art without undue experimentation.

FIGS. 14 and 15 show additional aspects of a clutch mechanism. Clutch 500 is similar to clutch 400 in that it has a central pivot 509, loop 501, and jaws 507. The jaws 507 of clutch 500, however, may be configured to provide a cradle 506 for syringe 502 and flange 503, in addition to gripping the threaded plunger 504 with threads or grooves 505. Clutch 500 may also include a locking mechanism 508 to hold the clutch in a closed or gripping position.

Clutch 600 is similar to clutch 420 in that it uses a crossover point to create bias. Clutch 600 may also have a clutch loop 601 and jaws 602, but the jaws 602 may be configured to provide a cradle 603 for syringe 607 and flange 606, in addition to gripping threaded plunger 605 with grooves or threads 604. Both clutch 500 and clutch 600 are compatible with a release button mechanism, similar in operation to those shown for cement gun 200 and clutch 300, as will be understood by one having ordinary skill in the art without undue experimentation.

While the disclosure has been described in terms of exemplary embodiments, those skilled in the art will recognize that the disclosure can be practiced with modifications in the spirit and scope of the appended claims. These examples given above are merely illustrative and are not meant to be an exhaustive list of all possible designs, embodiments, applications or modifications of the disclosure.

What is claimed is:

1. A method for dispensing biomaterial into a patient, said method comprising:
  providing biomaterial to a device configured to inject the biomaterial into a patient, the device comprising:
    a handle having a removable syringe positioned within the handle; and
    an engagement mechanism retained within the handle and moveable between an engaged position and a disengaged position, the engagement mechanism including a cutout with one or more grooves configured to mate with a portion of the syringe in the engaged position, and the one or more grooves do not engage with the syringe in the disengaged position,
  wherein engagement mechanism is retained in the engaged position by a locking mechanism,
  wherein the locking mechanism includes a locking pin and a spring, and
  wherein the locking pin has a flat portion at its uppermost end, and the flat portion fits into a groove in the engagement mechanism, thereby locking the engagement mechanism into place in the engaged position.

2. The method of claim 1, wherein the one or more grooves are located along one side of the cutout.

3. The method of claim 1, wherein syringe includes a plunger having threads configured to mate with the one or more grooves in the engaged position.

4. The method of claim 3, wherein the syringe includes no mating threads for the plunger.

5. The method of claim 1, wherein the engagement mechanism is slidable between the engaged position and the disengaged position.

6. The method of claim 1, wherein the engagement mechanism is mated with a spring to press or bias the engagement mechanism toward the disengaged position.

7. The method of claim 6, wherein the spring is retained with a retaining pin.

8. The method of claim 1, wherein the engagement mechanism is disengaged by using a release button to release the locking mechanism.

9. A method for dispensing biomaterial into a patient, said method comprising:
  providing biomaterial to a device configured to inject the biomaterial into a patient, the device comprising:
    a handle having a removable syringe with a plunger have a plurality of threads, the syringe positioned within the handle; and
    an engagement mechanism retained within the handle and moveable between an engaged position and a disengaged position, the engagement mechanism including a cutout with one or more grooves configured to mate with the plurality of threads of the plunger in the engaged position, and the one or more grooves do not engage with the plurality of threads of the plunger in the disengaged position,
  wherein the engagement mechanism is retained in the engaged position by a locking mechanism having a locking pin and a spring, the locking pin has a flat portion at its uppermost end, and the flat portion fits into a groove in the engagement mechanism, thereby locking the engagement mechanism into place in the engaged position.

10. The method of claim 9, wherein the engagement mechanism is disengaged by using a release button to release the locking mechanism.

11. A method for dispensing biomaterial into a patient, said method comprising:
providing biomaterial to a device configured to inject the biomaterial into a patient, the device comprising:
a handle having a removable syringe with a plunger positioned within the handle; and
an engagement mechanism retained within the handle and moveable between an engaged position and a disengaged position, the engagement mechanism including a cutout with one or more grooves configured to mate with the plunger in the engaged position, and the one or more grooves do not engage with the plunger in the disengaged position,
wherein the engagement mechanism is retained in the engaged position by a locking mechanism having a locking pin and a spring, the locking pin has a flat portion at its uppermost end, and the flat portion fits into a groove in the engagement mechanism, thereby locking the engagement mechanism into place in the engaged position.

12. The method of claim 11, wherein the engagement mechanism is disengaged by using a release button to release the locking mechanism.

13. The method of claim 11, wherein the engagement mechanism is mated with a spring to press or bias the engagement mechanism toward the disengaged position.

14. The method of claim 11, wherein the device further comprises:
a lid having a closed position and an open position, the lid configured to retain the syringe within the handle in the closed position, the lid further configured to release the syringe from the handle in the open position;
a hinge pin configured to attach the lid to the handle;
a lid pin located in a side of the lid and configured to fit into a corresponding hole in the handle, thereby retaining the lid in the closed position; and
a lid spring configured to press the lid in a direction substantially parallel to the lid pin, the spring further configured to retain the lid pin in its corresponding hole until released by a user of the device.

15. The method of claim 11 further comprising:
placing the syringe into the handle;
sliding the engagement mechanism to the engaged position to engage the plunger; and
dispensing biomaterial.

16. The method of claim 15 further comprising relieving injection pressure in the syringe by operating a release button.

* * * * *